Figure 1:
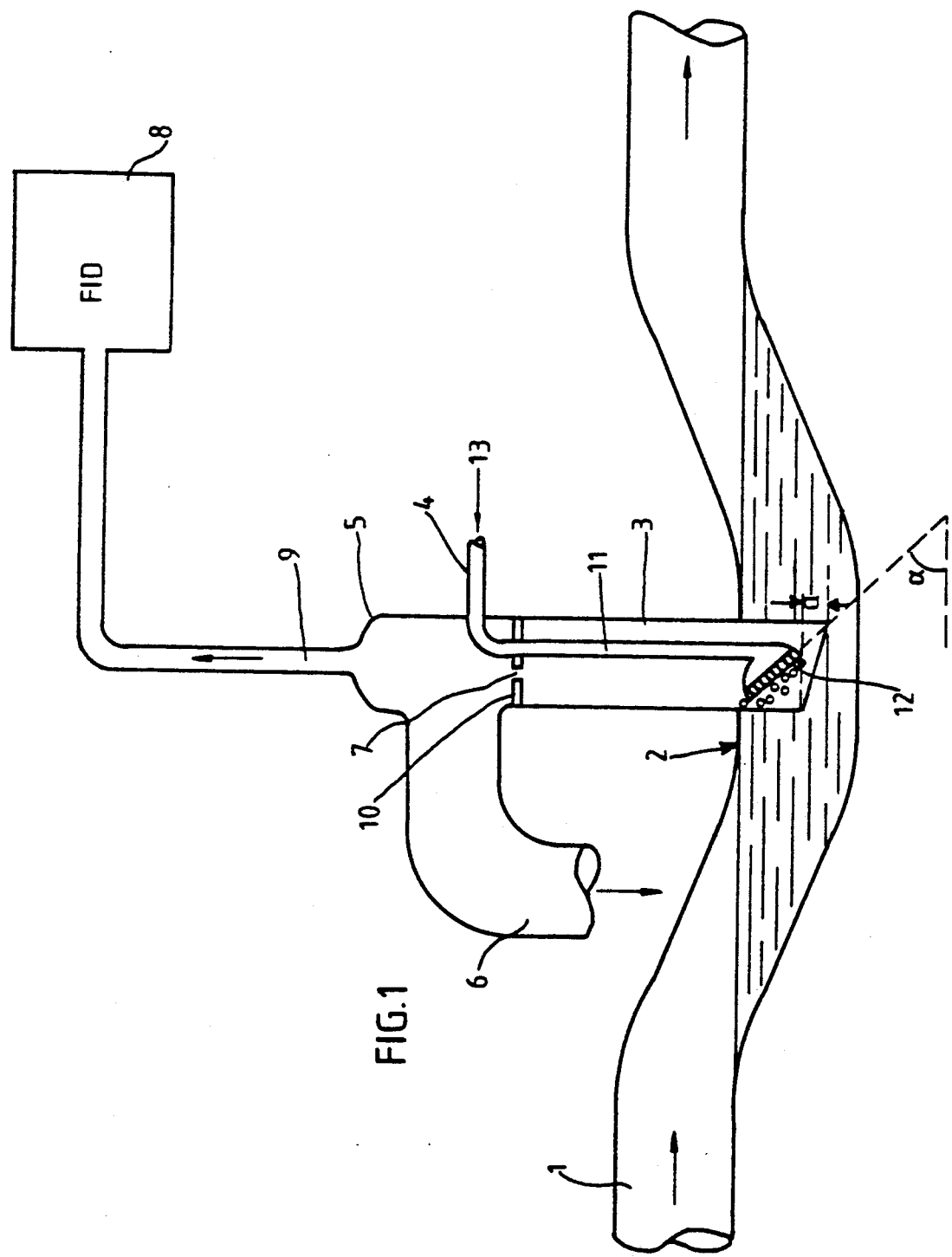

United States Patent [19]

Kahl et al.

[11] Patent Number: 5,127,259
[45] Date of Patent: Jul. 7, 1992

[54] APPARATUS FOR DETERMINING VOLATILE SUBSTANCES IN LIQUID

[75] Inventors: Melchior Kahl, Bergisch Gladbach; Dieter Kitzelmann, Bonn, both of Fed. Rep. of Germany

[73] Assignee: Bayer Aktiengesellschaft, Leverkusen, Fed. Rep. of Germany

[21] Appl. No.: 666,098

[22] Filed: Mar. 7, 1991

[30] Foreign Application Priority Data

Mar. 7, 1990 [DE] Fed. Rep. of Germany ....... 4007064

[51] Int. Cl.$^5$ .............................................. G01N 7/14
[52] U.S. Cl. ..................................................... 73/19.1
[58] Field of Search ................................ 73/19.1, 19.01

[56] References Cited

U.S. PATENT DOCUMENTS

| 4,330,385 | 5/1982 | Arthur et al. ............. | 73/19.1 X |
| 4,715,217 | 12/1987 | Coyne et al. ............. | 73/19.1 X |
| 4,731,732 | 3/1988 | Warchol et al. ........... | 73/19.01 X |

FOREIGN PATENT DOCUMENTS

| 17848 | 1/1982 | Japan ........................ | 73/19.1 |
| 14363 | 7/1986 | Japan ........................ | 73/19.1 |
| 913152 | 3/1982 | U.S.S.R. .................... | 73/19.1 |
| 1000847 | 2/1983 | U.S.S.R. .................... | 73/19.1 |

Primary Examiner—Hezron E. Williams
Assistant Examiner—Joseph W. Roskos
Attorney, Agent, or Firm—Sprung Horn Kramer & Woods

[57] ABSTRACT

The apparatus for determining volatile gases and/or vapor components in a flowing liquid consists basically of a gas analysis instrument (8) which is charged via a sampling tube (9) with the components to be measured which have been freed from the liquid. A carrier gas (17) is passed through a gas inlet tube (11) into the flowing liquid and liberates the gas components to be measured, which are then passed together with the carrier gas (13) through the sampling tube (9) to the gas analysis instrument (8). For this purpose the sampling tube (9) is connected to a dip tube (3) which projects into the liquid and surrounds a porous distributor body (12) for introducing the carrier gas (13) in the form of finely disperse gas bubbles, which distributor body is connected to the gas inlet tube (11) and is subjected to the flow of liquid from the side.

8 Claims, 1 Drawing Sheet

APPARATUS FOR DETERMINING VOLATILE SUBSTANCES IN LIQUID

The invention relates to an apparatus for detecting volatile constituents (gases or vapours) in water. The water to be analysed is here continuously passed through a phase changer (stripper), where the volatile constituents are stripped out by a carrier gas stream. The gas stream enriched with the substance is then passed to an analysis instrument which detects this substance.

For the early detection of the start of a sudden and unintentional emission of water-polluting substances in the cooling water or in the production effluents, analysis methods which can provide at least a qualitative early detection are of great importance.

A typical and therefore frequently occurring problem is the early detection of organic substances such as, for example, aromatic and aliphatic hydrocarbons, ethers, esters, alcohols, ketones, halogenated hydrocarbons and the like. Analysis methods which can measure the organic load in water are known. Automatic instruments measure, for example, the TC value (total carbon) by thermal/catalytic combustion of a small effluent sample to $CO_2$ in a pyrolysis furnace. The $CO_2$ concentration is then determined in an infrared analyser (See G.Axt: "An Instrument For Continuously Measuring The Organic Carbon In The Potable Water and Effluent Fields", *Wasser*, 36 (1969) pp. 328-339.)

It is also known to determine the organic load via the chemical oxygen demand (COD value). Continuous measurement methods for on-line analysis are also available for this purpose.

The disadvantage is that these instruments carry out a fairly involved analytical procedure and are therefore technologically expensive and maintenance-intensive. A further point is that the response times are in the range of several minutes, so that it is not possible to give a rapid alarm in the case of suddenly occurring leakages.

The object of this invention is a simplification of such a measuring device and an improvement in the response behaviour by combining a very fast analysis instrument with an effective stripping device. In the stripping device, the volatile organic substances are transferred from the aqueous phase into the gas phase.

It is known to effect the transfer of organic constituents into the gas phase by the head space method or by stripping devices and to determine the content of organic substances in this gas phase.

In the head space method, the equilibrium ratio of the concentrations of organic substances in water and the gas space above the latter is exploited in accordance with Henry's law. This method is frequently used in combination with a gas chromatograph, since only small quantities of the gas space to be analysed are present and also only small quantities are required for this analyser.

In the known stripping devices, for example, a closed carrier gas circulation is used for completely depleting the water of the organic constituents and either passing the gas stream directly to a gas chromatograph or, in the case of only small quantities, concentrating the organic substances in a cold trap or on an adsorber and then measuring this concentrated gas in the gas chromatograph by vaporisation or desorption respectively. (See, e.g., the following: T. Lang et al.: "Determination of Volatile Halocarbons in Water by Purged-Closed Loop Gas Chromatography", *Bull. Envision. Contam. Toxicol.*, 32 (4), pp. 429-438.; T. Okuno et al.: "Study On Measurements Of Low Boiling Point Chlorinated Hydrocarbons In Sea Water", *Hyogo-ken Kogai Kenkijusho Kenkyu Hkoku*, 10, pp. 8-14 and B. Dowty et. al: "Automated Gaschromatographic Procedure To Analyze Volatile Organics In Water and Biological Fluids", *Anal. Chem*, 48 (6), pp. 946-949.) The methods just mentioned are exclusively laboratory methods and allow only a discontinuous measurement.

A further laboratory method for determining hydrocarbons in water utilises hydrogen electrochemically produced in situ as the stripping gas with subsequent gas-chromatographic determination of the hydrocarbons in the vapour space of the sample (See, e.g. U.S. Pat. No. 3,927,987, issued Dec. 23, 1975 and U.S. patent application Ser. No. 525,430, filed Nov. 20, 1974.).

For continuous monitoring of water for highly volatile halogenated hydrocarbons, a stripping method is known in which air bubbles into the water through a tube with holes in the flow sensor with a syphon. The flow sensor is located in the water stream to be examined. The stripper air here bubbles in excess through the holes into the water and is thus enriched with the organic substances. A part of the gas is fed to an analysis instrument for determination of the organic substances.

It is a disadvantage of the existing method that, depending on the flow velocity of the water and depending on the water level in the flow apparatus, more or less stripping gas is entrained by the water stream. In the most unfavourable case, all the gas is entrained, so that no gas is available for analysis. A further disadvantage is that, in the event of blockages on the outflow side, water can pass through the holes into the gas line and thus into the gas analyser. Finally, depending on the water level in the flow sensor, the gas space above the water can be very large, so that gas which is not identical with the gas composition above the actual water sample is measured by the analysis instrument. This means, however, that the measured results are distorted.

The object of the present invention is an improvement of the spripping procedure in conjunction with a gas analysis instrument, for example, in the measurement of organic constituents in water with a view to rapid mass transfer with direct feeding of the actual stripping gas to the analyser, without the stripping procedure being adversely affected by the level of the flow fitting or by a high flow velocity in the apparatus.

Starting from a gas analysis instrument with a sampling tube leading to the liquid, this object is achieved according to the invention when the sampling tube is connected to a dip tube which projects into the liquid and surrounds a porous distributor body which is connected to the gas inlet tube and is subjected to the flow of liquid from the side. The carrier gas thus passes in the form of finely dispense gas bubbles via the distributor body into the liquid volume enclosed by the dip tube and, after bubbling through, completely flows off upwards. A part stream is continuously delivered to the analysis instrument for determining the components to be measured. The liquid volume through which the carrier gas bubbles is thus enclosed by the dip tube, so that a defined volume for mass transfer (stripping procedure) is available in the liquid.

Advantageously, the distributor body consists of a porous plate arranged at an angle to the direction of flow, whose angle of incidence is 30° to 85°, preferably 50° to 70°.

According to a preferred embodiment, the lower end of the dip tube is bevelled on the side facing the flowing liquid and its part located inside the flow pipe extends over at least two-thirds of the diameter of the flow pipe. This has the result that continuous exchange with liquid newly flowing in is possible even at low level in the flow pipe and, at the same time, contamination by solid particles in the water can be prevented as a consequence of the turbulence occurring in the dip tube.

It has also proved to be advantageous when the distance between the obliquely arranged distributor plate and the sloping underside of the dip tube is such that the liquid volume in the dip tube is small and a rapid exchange thus takes place. At the same time, this ensures that the carrier gas can rise relatively rapidly within the sampling tube. The height of the liquid level in the dip tube is essentially determined by the level in the flow pipe, if no back pressure on the downstream side has to be overcome. With a view to minimising the water volume through which the carrier gas must bubble, the distance a between the lower end of the distributor body and the lower end of the sampling tube is advantageously 0.5 cm to 1.5 cm.

In order to avoid penetration of the liquid into the gas feed line to the analysis instrument in the event of blockages on the outflow side or of a high back pressure in the piping system, the dip tube is advantageously provided with an overflow.

An embodiment has proved particularly suitable which consists of a combination of the stripping device described with a flame ionisation detector (FID) with a vacuum maintained on the gas side inlet thereof, so that the stripping gas is drawn in by the FID.

The invention achieves the following advantages:

The apparatus described allows continuous monitoring of vaporisable inorganic and organic substances in water, for example of solvents. In combination with a flame ionisation detector (FID) as a total carbon analyser, the response time is less than 10 seconds. The detection limit is dependent on the substance and depends on the volatility and the solubility in water. The hydrophobic hydrocarbons and the ecologically objectionable chlorinated hydrocarbons can be detected with particular sensitivity.

The detection limit for these substance groups is below 10 µl/l. The stripper/FID combination is thus superior to a TOC instrument also with respect to the detection sensitivity. Compounds which are not easily vaporised and salt-type compounds cannot be detected.

An illustrative example of the invention will be described in more detail below with reference to a drawing.

The sole FIGURE is a pictorial view of preferred apparatus for determining volatile substances in liquid in accordance with the present invention.

The liquid to be examined, for example water, flows here from the left to the right through a flow pipe 1 which forms a syphon 2. At the syphon 2, a dip tube 3 is installed perpendicular to the flow pipe 1. The lower end 4 of the dip tube 3 is bevelled in such a way that the inlet area of the dip tube faces the flow. The length of the obliquely flattened dip tube is such that even at a low level in the flow pip 1, rapid exchange with water newly flowing in is possible and, at the same time, contamination by solids fractions in the water is prevented as a consequence of the turbulence arising in the dip tube. In practice, this is accomplished when the part projecting into the liquid extends over more than two-thirds of the diameter of the flow pipe 1. At the top side of the dip tube 5, an overflow tube 6 branches off which, in the case of penetration of water via the orifice 7, ensures that the water flows off before it can reach the sampling tube 9 leading to the gas analyser 8. The gas analysis instrument is here a flame ionisation detector (FID). The FID is operated with a vacuum at its inlet, so that the gas component to be measured is drawn in through the sampling tube 9. An FID of this type of construction is described in German Patent Specification No. 2,932,436.

To prevent an excessive amount of water from rising in the water system in the event of a very high back pressure, a restrictor 10 having an orifice of 2 to 3 mm diameter (orifice 7) is provided to serve as a water barrier.

A gas inlet tube 11 having a porous distributor plate 12 in the oblique position is arranged inside the dip tube 3. The porous distributor plate can consist of a glass frit or sintered plate or of a wooden body. As an alternative, a fine punched screen can be used. The angle of incidence $\alpha$ of the distributor plate 12 (angle from the horizontal) should be at least 30°. A range between 50° and 70° has proved to be particularly suitable The exit area of the distributor body faces the flow; that is to say the perpendicular on the distributor surface has a component directed against the flow. The oblique position of the distributor plate 12 has here to be proved particularly advantageous, since in this way finely distributed non-coalescing gas bubbles are formed which lead to intensive stripping-out of the volatile components contained in the liquid stream (water).

The distributor plate 12 is located just above the bevelled dip tube end 4 and below the liquid level in the dip tube 3, which is determined in normal operation by the liquid level in the flow pipe syphon 2. Thus, the distance a between the lower end of the distributor plate 12 and the lower end of the dip tube 3 is 0.5 to 1.5 cm. Thus, a spatially limited, rapidly exchangeable water volume is available for the stripping process. This is of essential importance to a rapid response time of the FID 8, when the concentration of the gas component to be measured changes.

The carrier gas used normally is hydrocarbon-free atmospheric air. It is also conceivable to use other gases such as nitrogen, carbon dioxide or rare gases. The carrier gas 13 passes via the inlet tube 11 to the distributor plate 12 and rises there in the form of fine small gas bubbles enriched with the volatile constituents of the effluent stream. The gas mixture then flows through the orifice 7 of the water barrier 10 into the dip tube head 5. A part of the gas mixture is drawn in by the FID 8 through the sampling tube 9, while the excess part flows into the open through the overflow tube 6.

Using the apparatus described, effluent streams of between 30 and 300 1 per hour can be monitored on line. Carrier gas streams of between 30 and 100 1 per hour are used for this purpose.

MEASUREMENT EXAMPLE

Effluent mass flow 150 1 per hour.
Carrier gas flow (air) 100 1 per hour.
The measurement components to be examined consisted of chlorobenzene and dichloromethane vapours. At a substance concentration of 50 µl/l of dichloromethane, an organic carbon quantity of 320 mg/m³ was measured in the FID. The detection limit was 0.4 μl/l.

In the measurement of chlorobenzene, the substance concentration in the effluent stream was 5 μl/l. In the FID, an organic carbon quantity of 210 mg/m³ was measured. In this case, the detection limit was 0.3 μl/l. At an internal diameter of 4 mm of the sampling tube 9, the response time of the measuring device was 0.75 second/m of tube length. The response time of the FID 8 increases correspondingly with increasing length of the sampling tube 9. In operation in practice, a response time of 3 to 10 seconds can be achieved. All the measurements were carried out at room temperature.

There has thus been shown and described novel apparatus for determining volatile substances in liquid which fulfills all the objects and advantages sought therefor. Many changes, modification, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow:

We claim:

1. In an apparatus for determining volatile gas and/or vapor components in a flowing liquid, comprising a gas analysis instrument which is connected to the liquid via a sampling tube, an carrier gas bubbling through a gas inlet tube into the flowing liquid and thus stripping out the gas components which are to be measured and which are passed together with the carrier gas through the sampling tube to the gas analysis instrument, the improvement wherein the sampling tube is connected to a dip tube which projects into the liquid and surrounds a porous distributor body for introducing the carrier gas in the form of finely dispersed gas bubbles, wherein the distributor body is connected to the gas inlet tube on one side and is subjected to the flow of liquid on an opposite side; and wherein the distributor body comprises a porous element having said opposite side arranged at an angle to the direction of flow.

2. Apparatus according to claim 1, wherein the distributor body comprises a porous plate.

3. Apparatus according to claim 1, wherein the angle of incidence $\alpha$ of the opposite side of the porous distributor body is in the range of 30° to 85°.

4. Apparatus according to claim 1, wherein the lower end of the dip tube is bevelled on the side facing the flowing liquid and its part located inside the flow pipe extends over at least two-thirds of the diameter of the flow pipe.

5. Apparatus according to claim 1, wherein the distance a between the lower end of the distributor body and the lower end of the dip tube is in the range of 0.5 cm to 1.5 cm.

6. Apparatus according to claim 1, wherein the dip tube has an overflow.

7. Apparatus according to claim 1, wherein the gas analysis instrument comprises a flame ionisation detector having means for applying a vacuum on the gas side inlet thereof.

8. Apparatus according to claim 1, wherein the angle of incidence $\alpha$ of the opposite side of the porous distributor body is in the range of 50° to 70°.

* * * * *